(12) United States Patent
Pinto

(10) Patent No.: US 9,937,025 B2
(45) Date of Patent: Apr. 10, 2018

(54) DENTAL FLOSS PERIOSCOPE

(71) Applicant: Adolf Patrick Pinto, Richland, WA (US)

(72) Inventor: Adolf Patrick Pinto, Richland, WA (US)

( * ) Notice: Subject to any disclaimer, the term of this patent is extended or adjusted under 35 U.S.C. 154(b) by 153 days.

(21) Appl. No.: 15/089,433

(22) Filed: Apr. 1, 2016

(65) Prior Publication Data
US 2017/0281322 A1    Oct. 5, 2017

(51) Int. Cl.
*A61C 15/04*     (2006.01)
*A61B 5/00*      (2006.01)

(52) U.S. Cl.
CPC .......... *A61C 15/042* (2013.01); *A61B 5/4547* (2013.01); *A61C 15/04* (2013.01); *A61C 15/046* (2013.01); *A61B 5/0053* (2013.01); *A61B 5/4827* (2013.01); *A61B 5/4836* (2013.01)

(58) Field of Classification Search
CPC ..... A61C 15/042; A61C 15/04; A61C 15/041; A61C 15/045; A61C 15/046
USPC .................................................. 132/321, 323
See application file for complete search history.

(56) References Cited

U.S. PATENT DOCUMENTS

| | | | | |
|---|---|---|---|---|
| 4,633,892 A * | 1/1987 | Charatan | ............... | A61C 15/041 132/321 |
| 4,974,615 A * | 12/1990 | Doundoulakis | ...... | A61C 15/042 132/321 |
| 5,316,028 A * | 5/1994 | Flemming | ............ | A61C 15/043 132/321 |
| 5,545,480 A * | 8/1996 | Lalani | .................. | A61C 15/042 132/321 |
| 5,570,710 A * | 11/1996 | Wei | ....................... | A61C 15/043 132/321 |
| 5,765,577 A * | 6/1998 | Wei | ....................... | A61C 15/043 132/321 |
| 6,112,753 A * | 9/2000 | Arsenault | ............ | A61C 15/042 132/321 |
| 8,132,579 B1 * | 3/2012 | Wien | .................... | A61C 15/042 132/321 |
| 2006/0289032 A1 * | 12/2006 | Satary-Ravabakhsh | ................... | A61C 15/042 132/321 |
| 2008/0314406 A1 * | 12/2008 | Barrie | .................. | A61C 15/042 132/329 |
| 2011/0073131 A1 * | 3/2011 | Hsu | ........................ | A61C 15/00 132/323 |
| 2015/0122281 A1 * | 5/2015 | Martens | ............... | A61C 15/042 132/200 |
| 2015/0272711 A1 * | 10/2015 | Gagan | .................. | A61C 15/042 132/329 |

\* cited by examiner

*Primary Examiner* — Tatiana Nobrega

(57) ABSTRACT

This disclosure proposes a technique for finding and treating areas of tooth decay primarily below the gum line using protuberances provided in a length of modified dental floss. The length of modified dental floss is provided with protuberances which can be used to detect areas of tooth decay by the roughness and sensitivity felt as the length of modified dental floss glides over the area of tooth decay. Specially designed posts are used to anchor the ends of the length of modified dental floss in order to be able to apply greater force during flossing, and free up fingers that would normally have the dental floss wrapped around them, to guide the floss to the right locations for flossing.

1 Claim, 3 Drawing Sheets

DENTAL FLOSS PERIOSCOPE

FIELD OF THE DISCLOSURE

This disclosure relates to the treatment of periodontal disease. Traditionally, the treatment option for advanced stages of periodontal disease is gum surgery. Recently, an alternative nonsurgical method involving the use of miniaturized camera assisted visual monitoring to find and treat areas of tooth decay below the gum line, has been put into practice. The proposed invention also proposes a nonsurgical treatment for periodontal disease. However, instead of miniaturized video cameras, dental floss is modified with protuberances spaced along the length of dental floss. The protuberances are used to detect and treat areas of tooth decay. Two specially designed posts are provided to hold the modified dental floss taut between the posts, thus freeing up the fingers around which the dental floss would normally have been wrapped. The freed up fingers then can be used to better guide the dental floss, and the posts can be used to exert the additional force needed to push the protuberances in the modified dental floss into the regions below the gum line where decay is present, and work the floss more aggressively for more effective amelioration of the decay.

BACKGROUND OF THE DISCLOSURE

Gum disease was found to be responsible for personal health problems such as insomnia, poor digestion, arthritis, depression and gradual loss of lung capacity. It was observed that following dental cleaning in a dentist's office, in the near term, the health related problems were significantly reduced. This observation led to aggressive flossing and brushing, which for several years was able to keep the health problems in check. However, as periodontal disease progressed, dental bacteria eventually again asserted itself and health related issues again became a problem. Concurrently, it was observed that the onset of dental bacteria was food related. In general, the type and quantity of food intake and exercise had to be balanced with the level of mental tranquility at the time of food intake. An attempt was made to control the flare up of dental bacteria by following a restrictive diet, along with vigorous brushing and flossing. Dental bacteria however frequently reasserted itself because mental tranquility levels were difficult to maintain consistently, and the wrong type, or too much food was consumed. As periodontal disease progressed further, the ensuing health related problems resulting from dental bacteria, were not capable of being controlled by brushing and flossing. The present invention resulted from the dilemma faced in not being able to seek of a dental hygienist in a hurry to remove the dental plaque and alleviate the accompanying health related problems, every time there was a period of low mental tranquility, and or the wrong type or excessive quantity of food was consumed.

BRIEF SUMMARY OF THE INVENTION

This disclosure proposes the modification of dental floss by placing protuberances along a length of dental floss. The protuberances in the modified dental floss are used for the detection and treatment of areas of tooth decay. The sensitivity felt when a protuberance in the dental floss contacts an area where tooth decay is present, as the modified length of dental floss glides over it, locates the area of tooth decay. Working the protuberance against the area of decay then ameliorates the decay, and over time helps to control the progression of the decay. The two ends of a length of dental floss modified by the placement of protuberances of additional thickness are each anchored to a separate post. With the two posts held apart and the length of dental floss taut, any extra length of dental floss can be wrapped around one or both posts, such that the length of dental floss with protuberances between the two posts is of a convenient length for flossing.

BRIEF DESCRIPTION OF THE DRAWINGS

The upper portion of FIG. 1 shows a length of dental floss with protuberances of normal thickness (5) and protuberances of additional thickness (3) and (4). One end of the length of dental floss is labeled (1) and the other end (2). Protuberances of additional thickness (3) and (4) are shown adjacent to ends (1) and (2) respectively of the length of modified dental floss. Loop (6) is used to form a protuberance in the length of dental floss, and is shown at a location in the dental floss where a protuberance of normal thickness (5) is desired. In the lower portion of FIG. 1 lengths of modified dental floss are shown attached together to form a string of lengths of modified dental floss. The end of the first length of modified dental floss is shown connected seamlessly to the start of the next length of modified dental floss.

DETAILED DESCRIPTION OF THE INVENTION

Figure 1:
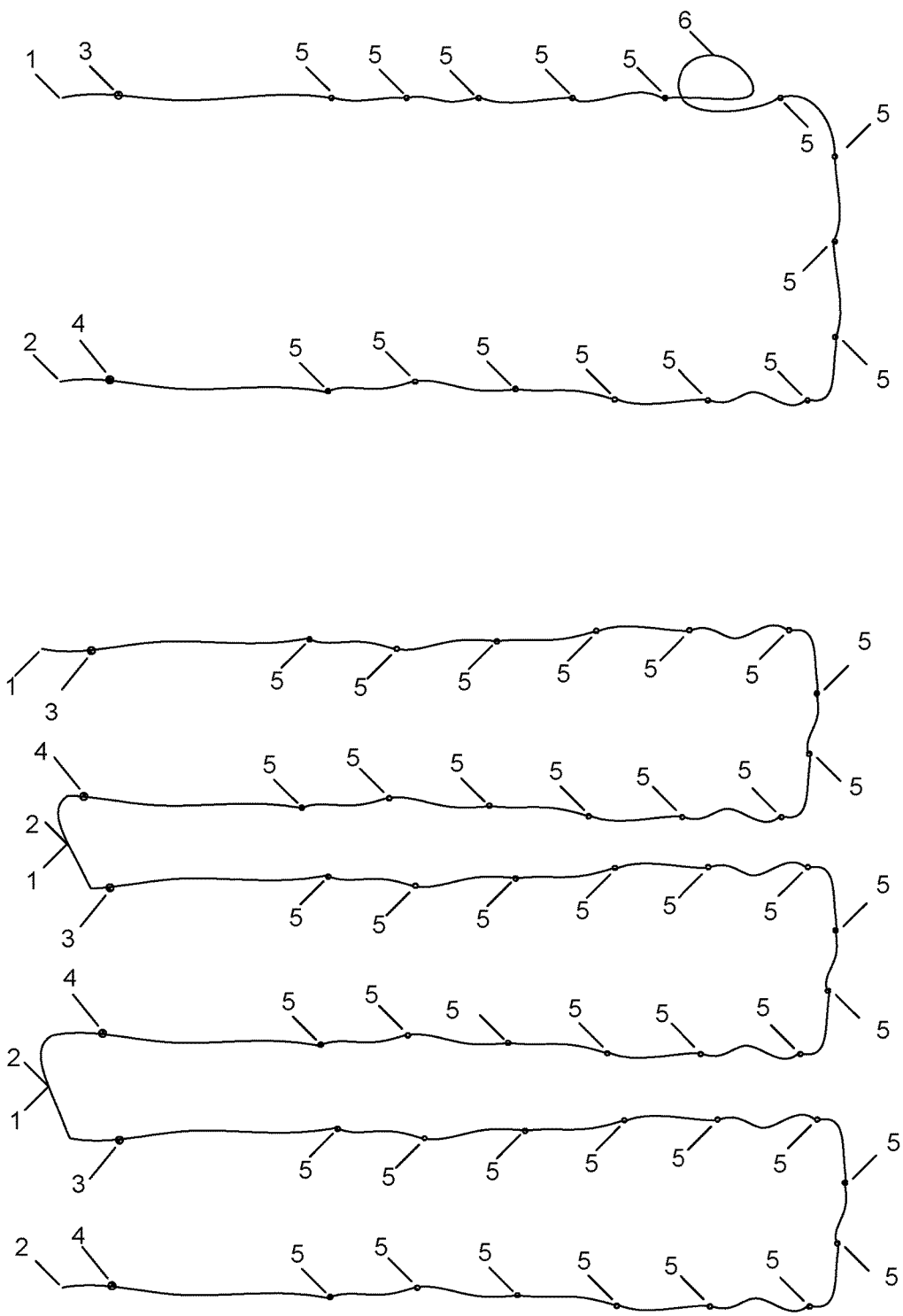

FIG. 1 shows the length of dental floss with protuberance of additional thickness (3) adjacent to end (1) and protuberance of additional thickness (4) adjacent to end (2). Protuberances of normal thickness (5) are shown spaced approximately equidistant from each other, and located between protuberances of additional thickness (3) and (4). End (1) is considered the start of the length of modified dental floss, and end (2) is considered the end of the length of modified dental floss. One of several methods may be used to create protuberances of normal thickness (5), and protuberances of additional thickness (3) and (4). The method used in this invention disclosure is to make a knot at the desired location in the length of dental floss where the protuberance is desired. A loop (6), as shown in the top portion of FIG. 1, is made at the location where the protuberance is desired and one of the ends (1) or (2), whichever is convenient, is passed through loop (6) in the direction in which a knot will be formed. The two ends (1) and (2) of the length of dental floss are then pulled apart to close loop (6) and form a knot which is a protuberance of normal thickness (5) at the location where loop (6) was initially made. Protuberances of normal thickness (5) are made by passing one of the ends (1) or (2) through loop (6) once prior to pulling the ends (1) and (2) apart. To make protuberances of additional thickness (3) and (4), one of the ends (1) or (2) of the length of dental floss is passed through loop (6) several times, four to five times is found to work best, instead of just once, prior to pulling the two ends (1) and (2) apart to close loop (6).

Figure 3:
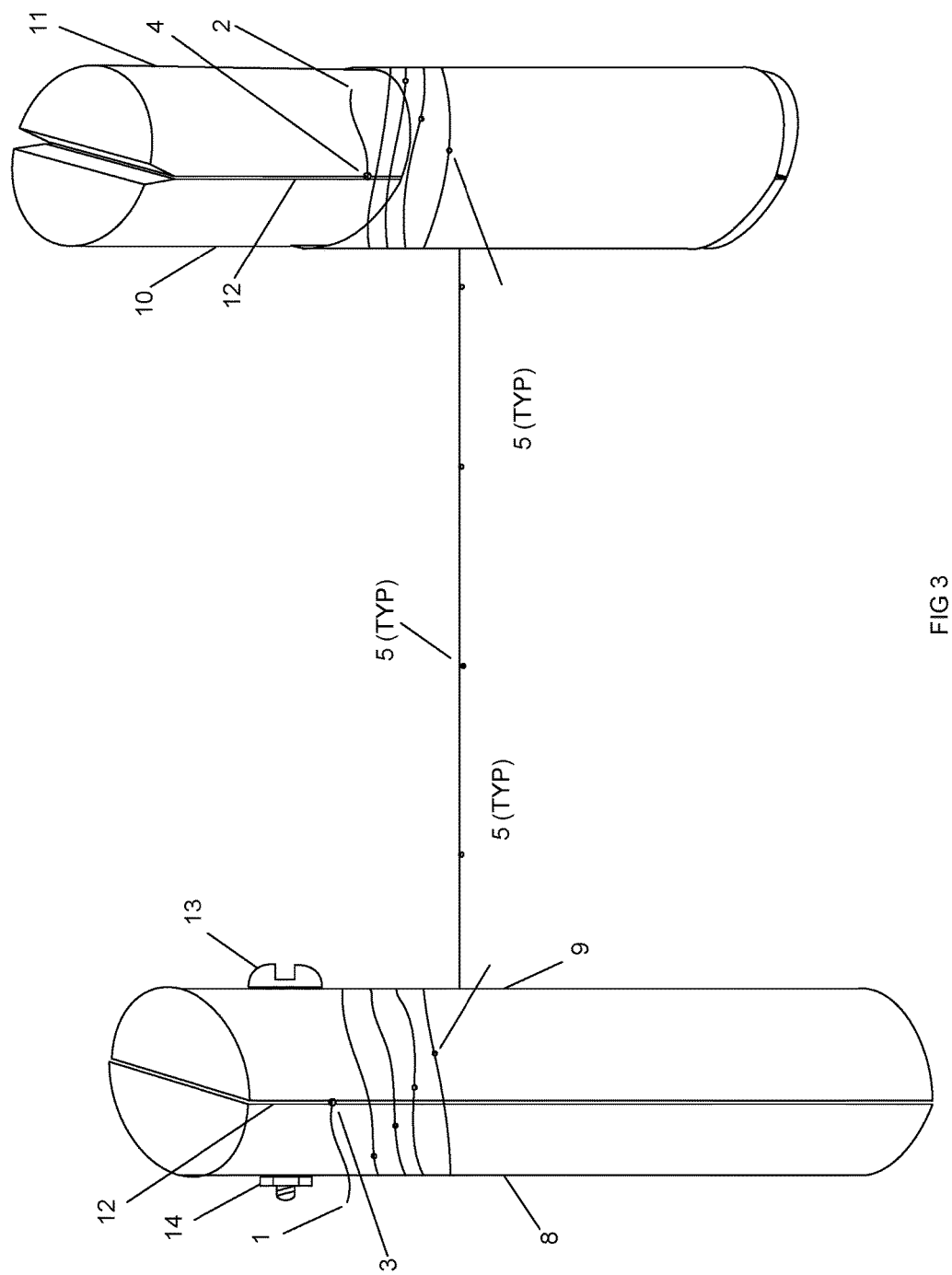
FIG. 3 shows the ready to floss assembly with the installation of the length of dental floss onto the posts (7). The assembly is shown with the post (7) assembled using a bolt (13) and nut (14) to the left and post (7) formed by taping (15) to the right. The excess length of modified dental floss is shown wrapped around one of the posts (7) and the remaining excess length of dental floss is shown wrapped around the other post (7).

In the lower portion of FIG. 1 three lengths of dental floss modified with protuberances of normal thickness (5) and additional thickness (3) and (4) are shown connected end to end to form a string of three lengths of modified dental floss. The three length string is shown to depict how a long string of modified dental floss is fabricated, with the trailing end of each of the lengths of modified dental floss connected seamlessly to the start of the next length of modified dental floss in sequence, until the very last modified length of dental floss is reached. Lengths of modified dental floss would need to be connected into a long string of modified dental floss for commercial purposes. In the event the lengths of modified dental floss are commercially manufactured for sale, a different method of making the protuberances may be devised. The long string of modified dental floss would then be placed in dental floss dispensing packaging as dental floss is currently sold. The end user would then pull out one length of modified dental floss, cut it between the first two successive protuberances of additional thickness (4) and (3) encountered, and place the length of modified dental floss from the dispenser onto two posts (7) as shown in FIG. 3. The two posts may be identical or different as long as they can successfully anchor the ends of the length of dental floss. The length of modified dental floss between the two posts will then be reduced to a convenient length for flossing by rotating each post (7) around its own axis.

Figure 2:
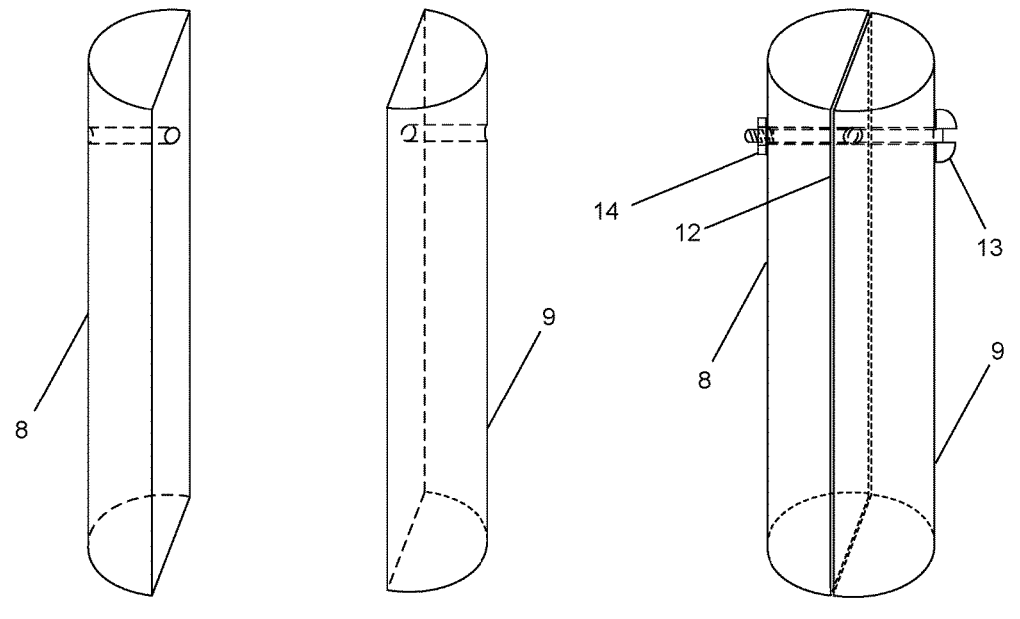
FIG. 2 depicts two types of posts (7) used to anchor each end of the length of modified dental floss. Post (7) in the upper portion of FIG. 2 is fabricated using a bolt (13) and a nut (14) to hold two identical semi-cylindrical bars (8) and (9) together. Post (7) in the lower portion of FIG. 2 is fabricated using tape (15) to hold two identical semi-cylindrical bars (10) and (11) together. In both types of posts (7), slot (12) can be seen between the two identical semi-circular bars (8) and (9) or (10) and (11).
Figure 2:
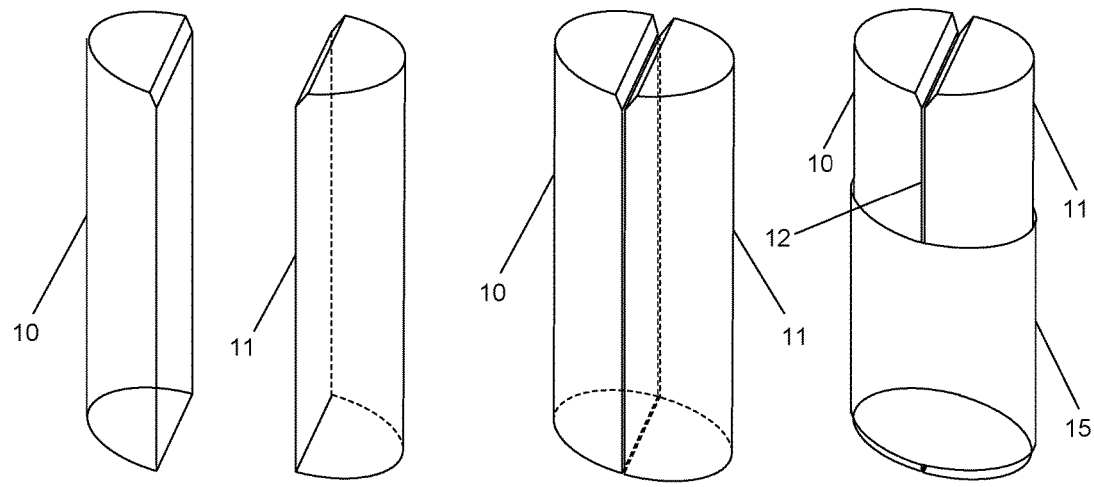

FIG. 2 depicts two types of posts (7) used to anchor each end of the length of modified dental floss at the location of the protuberance of additional thickness (3) and (4). The post (7) shown in the upper portion of FIG. 2 is fabricated by cutting a wooden cylinder, approximately one half inch in diameter and approximately 5 inches long in half lengthwise, to obtain two identical semi-cylindrical bars (8) and (9). The two identical semi-cylindrical bars (8) and (9) are shown to the left in the upper portion of FIG. 2. To the right of the upper portion of FIG. 2 is shown the two semi-cylindrical bars (8) and (9) joined together with bolt (13) and nut (14) to form one of the two types of post (7) proposed in this disclosure. The two identical semi-cylindrical bars (8) and (9) are placed facing each other, with their two rectangular flat surfaces touching each other and a hole is drilled through them at their upper ends. The two semi-cylindrical bars (8) and (9) are then attached by passing a bolt (13) though the hole and placing a nut (14) at the end of the bolt (13). Slot (12) is the space between the two semi-cylindrical bars (8) and (9). In order to open slot (12) in this type of post (7), the two semi-cylindrical bars (8) and (9) are swiveled around bolt (13) in opposite directions. One end portion of the length of modified dental floss between, a protuberance of additional thickness (3) or (4) and the first adjacent protuberance of normal thickness (5) next to the protuberance of additional thickness (3) or (4), is placed between the opened up portions of the semi-cylindrical bars (8) and (9), and the semi-cylindrical bars (8) and (9) are swiveled back. The end of the length of modified dental floss becomes anchored to post (7) when the length of modified dental floss is pulled taut and the protuberance of additional thickness (3) or (4) tries to go through but is restrained by slot (12).

The second type of post (7) used to anchor each end of the length of modified dental floss at the location of the protuberance of additional thickness (3) and (4) is shown in the lower portion of FIG. 2. The second type of post (7) is fabricated by cutting a wooden cylinder, approximately one half inch in diameter and approximately 4 inches long in half lengthwise, to obtain two identical semi-cylindrical bars (10) and (11). The two identical semi-cylindrical bars (10) and (11) are chamfered at the upper ends of their rectangular flat facing surfaces, for ease of sliding the length of modified dental floss into slot (12), after the two semi-cylindrical halves (10) and (11) are placed together, with their two rectangular flat surfaces facing and touching each other, and approximately half of their lower portions are joined together using tape (15) to form post (7). The top half of the assembled post (7) that is not taped has slot (12). The portion of the modified length of dental floss between the protuberance of additional thickness (3) or (4) and the protuberance with normal thickness (5) that is next to the protuberance of additional thickness (3) or (4) is inserted into slot (12) of posts (7). The taped joining of the two semi-cylindrical bars (10) and (11) has enough 'give' to let the portion of dental floss be inserted into slot (12).

In a commercially produced post (7) of the second type it is envisioned that the posts will consist of bars of a suitable material in which a narrow slot (12) can be cut using a water jet, laser or other suitable cutting method. The material selected for making the posts would have sufficient elasticity to permit the slot (12) to expand and permit the end of the modified dental floss to be inserted, and then spring back to restrain the protuberance of additional thickness (3) or (4) from going through slot (12) when the length of modified dental floss is pulled taut.

Working

After both ends of the length of modified dental floss are anchored, one end to one post (7) and the other end to another post (7), the two posts (7) are held apart to make the length of modified dental floss between the posts (7) taut. The length of modified dental floss will become taut because the protuberances with additional thickness (3) and (4) cannot pass through the slots (12) of the posts (7) and will become anchored to the posts (7). With the length of modified dental floss held taut, one or both of the two posts (7) are each rotated around their individual axes to make portions of the additional length of modified dental floss wrap around the two posts (7). The wrapping of portions of the length of modified dental floss around one or both posts (7) is continued until the length of the modified dental floss remaining taut between the two posts (7) is reduced to an optimum length for flossing. FIG. 3 shows the assembly with the installation of the length of dental floss onto the two posts (7). The length of modified dental floss between the two posts is shown reduced to a convenient length for flossing by the wrapping of a portion of the length of modified dental floss shown wrapped around both posts (7).

The reason for providing several protuberances in the length of modified dental floss is that with use the protuberances of normal thickness (5) become frayed, and with continued flossing using the frayed protuberance, the length of modified dental floss will break where it has become frayed. After the protuberance of normal thickness (5) that is being used becomes frayed, and before the length of the modified dental floss breaks at the protuberance of normal thickness (5) that is being used, the user selects another protuberance of normal thickness (5) to work against the area of tooth decay, for economical and optimal use of the length of modified dental floss.

The protuberances of normal thickness (5) in the dental floss are able to detect areas of tooth decay because of the sensitivity felt when the protuberances of normal thickness (5) are worked over the areas of tooth decay. The frictional force applied by the protuberances of normal thickness (5) on the areas of tooth decay is able to gradually remove the tooth decay. Performing perioscopy on oneself does control dental bacteria and helps in the gradual alleviation of periodontal disease. The proposed modified dental floss with protuberances can be used to detect areas where decay is present and gradually work them away. It has been observed that some degree of force needs to be applied to get the protuberances of normal thickness (5) into regions below the gum line to contact and remove decay. By performing the perioscopy on oneself one has that feed-back loop, and one can feel the roughness on the surface of the tooth the protuberance is rubbing against, indicating the presence of decay. Additionally, one can apply just so much force as to make the pain bearable, since the procedure is not without some degree of pain. The feed-back feature of the modified dental floss perioscope makes it exceptionally suitable and efficacious for the treatment of advanced periodontal disease.

What is claimed is:

1. A dental flossing system for performing a perioscopic procedure, the system consisting of:
   a) a segment of dental floss having:
      a first leading end and a second trailing end opposite the first leading end,
      a first protuberance positioned adjacent the first leading end and a second protuberance positioned adjacent the second trailing end;
      a plurality of protuberances interspaced evenly along a length of the segment of floss between the first and second protuberances;
      wherein the first and second protuberances have a same first thickness and each protuberance of the plurality of protuberances has a same second thickness, where the first thickness is larger than the second thickness and the first and second protuberances and the plurality of protuberances are formed by making knots in the segment of dental floss;
   b) a first and second post for tying the segment of dental floss, each post having two halves joined together via a connection means, where in use, the halves are separated and a portion of the segment of dental floss between the first protuberance and the plurality of protuberances is placed between the halves of the first post and a portion of the segment of dental floss between the second protuberance and the plurality of protuberances is placed between the halves of the second post, the halves of each post are fastened together by the connection means to secured the segment of dental floss to the posts such that the first and second protuberances remain external to the posts preventing the segment of dental floss from becoming disengaged from the posts.

* * * * *